United States Patent [19]

Spielmann

[11] Patent Number: 5,650,325
[45] Date of Patent: *Jul. 22, 1997

[54] APPARATUS HAVING A ROTATABLE STACK OF PARALLEL TRAYS WITH CULTURING SURFACES ON OPPOSITE SIDES FOR LIQUID/GAS EXCHANGE

[76] Inventor: Richard Spielmann, Rue d'Herinnes 43, B-7850 Enghien, Belgium

[*] Notice: The term of this patent shall not extend beyond the expiration date of Pat. No. 5,432,087.

[21] Appl. No.: 487,449

[22] Filed: Jun. 7, 1995

Related U.S. Application Data

[63] Continuation-in-part of Ser. No. 64,098, filed as PCT/BE91/00084, Nov. 11, 1991, Pat. No. 5,432,087.

[30] Foreign Application Priority Data

Nov. 29, 1990 [BE] Belgium .................. 90-01137

[51] Int. Cl.[6] ............... C12M 1/14; C12M 1/10; C12M 3/04; C12N 5/00
[52] U.S. Cl. ............... 435/299.1; 435/240.23; 435/289.1; 435/298.2; 435/299.2
[58] Field of Search ............ 435/240.23, 284, 435/285, 286, 310, 312, 289.1, 298.2, 299.1, 299.2

[56] References Cited

U.S. PATENT DOCUMENTS

| | | | |
|---|---|---|---|
| 3,839,155 | 10/1974 | McAleer et al. | 435/285 |
| 3,925,165 | 12/1975 | Muller | 435/312 X |
| 4,310,630 | 1/1982 | Girard et al. | 435/312 X |
| 4,912,058 | 3/1990 | Mussi et al. | 435/285 |
| 5,270,205 | 12/1993 | Rogalsky | 435/312 X |

FOREIGN PATENT DOCUMENTS

| | | |
|---|---|---|
| LU51646 | 7/1966 | Belgium . |
| 2354554 | 6/1977 | France . |
| 1539263 | 1/1979 | United Kingdom . |
| 2055397 | 3/1981 | United Kingdom . |
| 8800235 | 1/1988 | WIPO . |

*Primary Examiner*—David M. Naff
*Attorney, Agent, or Firm*—Leighton K. Chong

[57] ABSTRACT

An apparatus for providing an enhanced liquid/gas exchange surface such as during call culturing has an enclosed housing, a set of trays arranged in parallel inside the housing with a regular spacing between them, each of the trays being formed with a planar base, first rims on longitudinal sides and second rims on transverse sides of the trays projecting on both sides of the base so as to form retaining basins for retaining reaction liquid on both sides of the base as the trays are rotated through horizontal positions. In a preferred embodiment, the trays are stacked and have their first rims welded together to form the housing walls, while the second rims have a height lower than the first rims to create apertures between trays for fluid flow among the trays when they are rotated. The bases of the trays can have cutout portions on opposing transverse sides for the flow of reaction liquid from one side to the other. The trays can be fixed together to rotate inside a stationary housing, or can be mounted to inner walls of a rotatable housing. In a further embodiment, the trays have reduced-height second rims which are positioned at one lateral end with respect to the rotational axis to allow full drainage of fluid from that lateral end.

12 Claims, 9 Drawing Sheets

5,650,325

APPARATUS HAVING A ROTATABLE STACK OF PARALLEL TRAYS WITH CULTURING SURFACES ON OPPOSITE SIDES FOR LIQUID/GAS EXCHANGE

This patent application is a continuation-in-part of U.S. patent application Ser. No. 08/064,098 of the same inventor, entitled "Apparatus For Forming A Revolving Exchange Surface", filed May 20, 1993, now issued as U.S. Pat. No. 5,432,087, which was based upon PCT International Application BE 91/00084, filed Nov. 11, 1991.

FIELD OF THE INVENTION

The invention relates to an apparatus having an exchange surface that is cycled periodically between contact with a liquid phase and with a gas phase. An apparatus of this type is intended, for example, for culturing cells or the production of biological substances.

BACKGROUND ART

In industries producing vaccines by means of cell culture or producing biological substances secreted either by adherent or suspension cells or by microorganisms, use is made of microcarriers, roller bottles, Roux flasks, multiple chambered systems, and fermentors.

Microcarriers are small microscopic beads on which adherent cells are caused to grow. The beads are maintained in suspension in a culture medium, hereafter called the liquid phase, and with the help of a stirring system, the liquid phase is moved in contact with a gas phase. Everything is contained in a tank called a fermentor. This technique frequently used in the vaccine industry is nonetheless confronted with two major difficulties: (i) carrying out a suspension of microcarriers in a culture medium which is compatible with cell anchorage and growth conditions; and (ii) ensuring the control and stability of the culture medium pH, taking into account the fact that the exchange surface between the gas phase and the liquid phase is substantially limited.

Fermentors are also used for the culture of suspension cells or microorganisms. The handling difficulties are similar to those encountered during cultivation with a microcarrier. As the exchange surface between the gas phase and the liquid phase is limited by the fermentor diameter, the pH stability becomes extremely difficult to ensure.

Roller bottles are generally of cylindrical shape and are designed to be rotatable about their axes. The interior surface of the bottle is intended for cultivating adherent cells thereby forming a culture surface. The liquid culture medium is introduced into the bottle together with the cells. Rotation of the bottle allows the culture surface to be covered with a film of the culture medium thereby allowing cell growth on the culture surface. The culture surface is therefore limited to the size of the bottle. If the production of a large quantity of cells is desired, a large number of bottles will be necessary. This is the case for industries producing, for example, interferon, insulin, viral vaccines, or lymphokines. The handling of numerous bottles during inoculation, medium change, virus introduction, supernatant, and cell harvesting increases the risk of bottle and content contamination and requires the use of a significant number of staff. Many apparatuses have been developed to increase the culture surface of roller bottles by increasing the surface of the bottle itself. These known apparatuses are intended for developing adherent cell culture but are not intended for providing a homogeneous suspension of microcarriers or of suspension cells.

Roux flasks have been used for more than a century for producing viruses, as well as other biological substances. They have the same drawbacks as roller bottles, that is to say a limited culture surface per bottle and require a significant number of staff for handling.

In European Patent Application 0,345,415, a bottle apparatus is disclosed having an enlarged culture surface obtained by providing the bottle body with corrugations which extend axially or longitudinally relative to the bottle axis. This bottle does not, however, allow liquid stirring, and therefore it does not permit cultivation with microcarriers.

The surface used for cell development is also increased in an apparatus disclosed in U.S. Pat. No. 3,839,155 of McAleer et al. through a parallel arrangement of discs closely spaced along the bottle axis. This apparatus however is not entirely satisfactory for adherent cells because the trays, when rotated through a horizontal position, cannot retain a volume of liquid containing the cell suspension. This causes the liquid to quickly run out from the discs which does not favor cell attachment during cultivation. Moreover, this apparatus is not appropriate for the cultivation of so-called non-adherent cells because nothing is provided therein for stirring of the liquid phase.

In Luxembourg Patent Application 51,646 of Kamphans, a cell culture apparatus is shown comprising a set of parallel trays placed one above the other so as to form culture chambers. The trays are placed inside a housing which can be turned around an axis. This system permits cultivation of adherent cells on one side of the trays only. The interior surface is not used as a culture surface. Moreover, the housing does not permit the introduction of a stirring system for allowing microcarriers or microorganisms to be maintained in a homogeneous and continuous suspension.

In U.S. Pat. No. 3,925,165 of Muller, another apparatus is disclosed provided with radially-arranged vanes extending longitudinally inside a container which are continuously rotated through a gas phase at an upper part of the container and a reaction liquid in the lower part of the container. However, the vanes in this apparatus do not retain reaction fluid for an extended interval of time and therefore are not suitable for use in effectively culturing adherent cells.

SUMMARY OF THE INVENTION

The present invention aims to remedy the above drawbacks of the prior art. A principal object of the invention is to provide an apparatus that has a substantially increased surface area for culturing adherent cells thereon and can retain reaction liquid on the culturing surface for an interval of time sufficient for effective cell anchoring and cultivation. It is a further object that the apparatus also be suitable for culturing non-adherent suspension cells by stirring them in contact with gas and liquid phases. Another object is to provide a structure which can be assembled easily, stably, and at a low manufacturing cost per unit.

An apparatus according to the present invention comprises an enclosed housing for holding a reaction liquid and a gas phase therein, the housing having longitudinal and transverse sides, a set of trays arranged in parallel inside the housing with a regular spacing between them, each of said trays having (i) a planar base with lateral edges on opposing longitudinal and transverse sides thereof, (ii) first retaining rims extending continuously around at least said opposing longitudinal sides of the planar base and projecting a given height in a direction normal to the plane of the base, and (iii) second retaining rims continuing from said first retaining rims and positioned on said opposing transverse sides of the planar base and projecting a given height in the same direction normal to the plane of the base so as to define with said first retaining rims a shallow volume for retaining reaction liquid on a respective planar side of the planar base for an interval of time when the tray is rotated through a horizontal position, and driving means coupled through the housing for rotating the set of trays through the reaction liquid and gas phase.

In the preferred embodiments, the second rims have a height which is lower than the first rims. In this manner, the trays can be arranged in a stacked configuration with the height of the first rims defining a spacing between adjacent trays, while the lower height of the second rims define apertures that allow the flow of reaction liquid out from the lateral sides of the trays as they are rotated. The bases of the trays can have cutout (indented) portions formed on any of their opposing sides to allow reaction liquid to flow easily from one planar side of the trays to the other.

The trays may be fixed together to form a rotating body inside a stationary housing, or can be mounted to inner walls of the housing to be rotated together therewith. Alternatively, the housing can be constituted by stacked trays having abutting first rims that are sealingly welded together so as to eliminate the need for a separate housing part. Preferably, the trays have rims on both opposing planar sides of the base so that both sides can retain reaction liquid, thereby increasing the amount of usable culturing surface area. The trays may be rotated on a longitudinal or a transverse axis by any known driving means.

Owing to the layout and use of two sides of the proposed trays according to the invention, the exchange area or culture surface area is considerably increased for a given total volume of apparatus, thereby enhancing the culturing of adherent cells or microorganisms. Liquid/gas contact for a suspension of non-adherent cells, microorganisms, microcarriers or microspheres is also ensured without having to use any internal stirring system. The rotation of the trays provides excellent stirring of the liquid phase in the apparatus by the liquid being carried along by and moved over the rotating trays. This stirring and the liquid movement within the housing obtained by the rotation of the trays provides a homogeneous distribution of the liquid phase and greatly increases the exchange and culture efficiency. The apparatus of the invention can also be adapted to other uses requiring continuously cycled gas/liquid exchange surfaces, such as for an evaporator.

Exemplary embodiments of the invention are described in further detail hereinafter, with reference to the appended drawings:

DETAILED DESCRIPTION OF THE INVENTION

Generally, an apparatus according to this invention consists of an enclosed housing which defines a volume for containing a reaction liquid, a gas phase, and a set of planar trays arranged longitudinally inside the housing with a regular spacing between them. The set of trays is mounted to inner walls of the housing for rotation together therewith, or attached to a frame or connected to each other for rotation as a unit within a stationary housing. They may be rotated on a longitudinal or a transverse axis by any driving means as is known per se. Along their sides the peripheral edges of the trays have raised rims which project from the plane of the tray from one planar side or from both opposing planar sides of each tray in such a way as to act as a retainer element for the reaction liquid in which the trays are dipped during their rotation.

Described below are several exemplary embodiments of an apparatus in accordance with the invention. The described embodiments are configured for use as a rotating bioreactor intended to allow the culturing of adherent or non-adherent cells with or without microcarriers, or the culturing of bacteria and other microorganisms. Particularly for culturing adherent cells, for example, a liquid culture medium is introduced into the bioreactor housing to breed and grow the desired cells or microorganisms on the opposite sides of the trays and on the internal walls of the housing. In order to enhance culture performance, it is necessary to increase the available surface area susceptible of entering into contact with the reaction liquid and equally to maximize its exploitation.

Figure 1A:
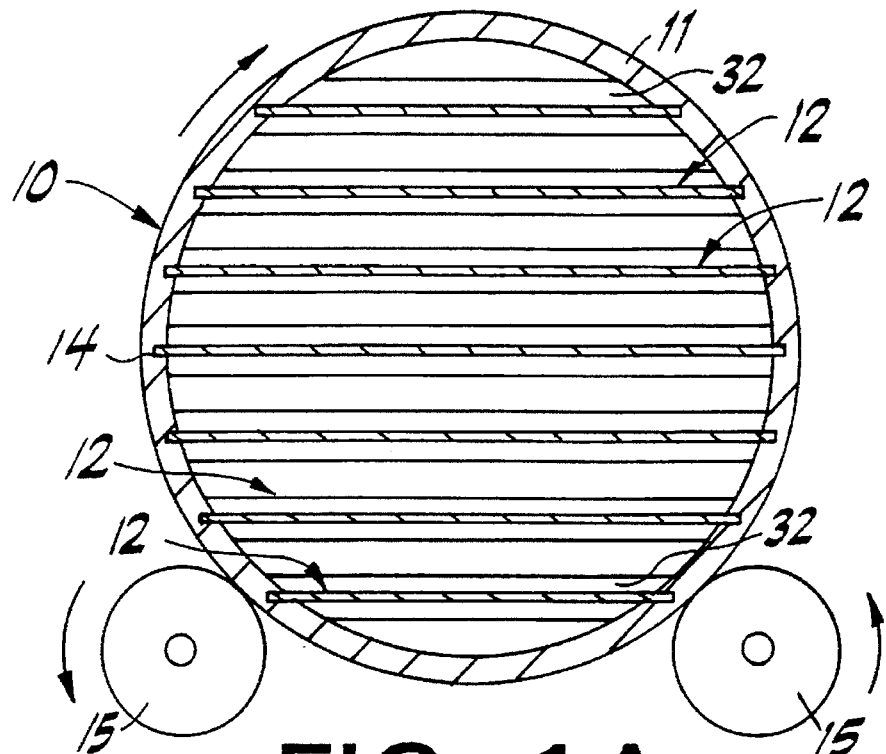
FIG. 1A is a front cross-sectional view of an embodiment of the invention having spaced parallel trays attached to a rotatable housing.
Figure 1B:
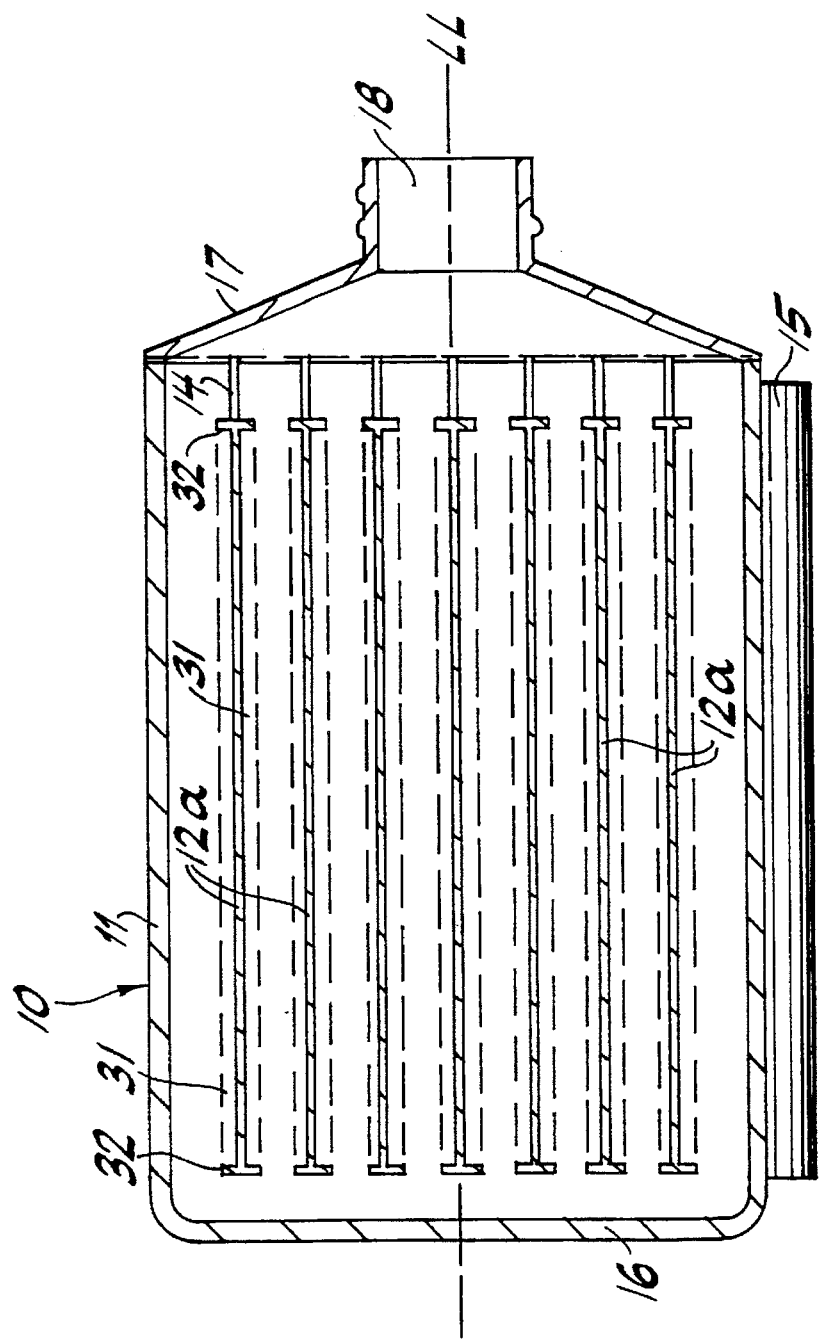
FIG. 1B is side cross-sectional view thereof.

The exemplary embodiment shown in FIGS. 1A and 1B is a rotating bioreactor 10 in the shape of a flask comprising an external cylindrical housing 11, which is mounted on rollers 15 which are to be driven into rotation around the longitudinal axis LL. At its opposed ends, the housing 11 has a base 16 and a neck 17. The neck has a bottle neck 18 which extends concentrically to the longitudinal axis LL of the housing and which serves to accomodate a closing means such as a screw cap. Inside the housing, the trays 12 are arranged in parallel extending in the longitudinal direction with a regular spacing between them. The trays 12 extend substantially the whole length of the housing up to a predetermined distance from the aforementioned base 16 and neck 17. The trays 12 may however be shorter in length. The trays 12 are constituted by a planar base sheet 12a which has a substantially rectangular shape, and are normally rigid so that they can support their own weight as well as the weight of liquid which they are intended to retain, as described further herein. The number and spacing of the trays can vary as a function of the technical characteristics of the apparatus.

The embodiment illustrated in FIGS. 1A and 1B has the trays 12 fixed by their opposing longitudinal edges to the inner surface of the housing 11. To this end, the inner surface of the housing 11 has longitudinal grooves 14 in which the longitudinal edges of the trays are securely fixed. The grooves 14 extend substantially the entire length of the housing 11.

The trays have a construction wherein their lateral edges on opposing longitudinal and transverse sides are provided with raised retaining walls or rims 31 (longitudinal sides) and 32 (transverse sides) which have a projecting height in a direction normal to the plane of the base sheets 12a. However, in this embodiment, since the longitudinal edges of the trays are fixed to the inner walls of the housing, the raised retaining walls of the trays on the longitudinal sides are constituted by the inner walls of the housing themselves. Each tray together with the aforementioned raised rims substantially form a retaining basin with a shallow volume that is able to retain temporarily a determined quantity of the reaction liquid contained in the housing as they are dipped therein and rotated through a horizontal position. The trays have rims on both opposing planar sides of the base so that both sides can retain reaction liquid, thereby increasing the amount of usable culturing surface area. Although the trays are shown arranged for rotation on a longitudinal axis, it is to be understood that they may instead be arranged for on a transverse axis.

The trays generally have a planar surface. However, with the aim of enlarging the total culture surface of the tray, the trays may have a wavy or corrugated surface contour. This further increases the development of the reaction or exchange surface and makes cell or microorganism culture very efficient.

The inner surface of the housing 11 as well as each of the opposite planar sides of the trays are treated for cell culture either before assembling, during partial assembling or even when the apparatus is completely assembled with the purpose of obtaining an optimal surface treatment compatible with the nature of the substance or microorganism to be adhered or cultivated thereon.

When assembling the apparatus, before hermetically attaching the base 16 to the housing 11, the trays 12 are slid inside the housing 11 in the grooves 14 in the inner surface thereof. The foregoing is a description of only one way of assembling the apparatus only. The trays can also be fitted in the housing by having their transverse edges held in grooves in the inner surfaces of the base 16 and another closure wall on the opposite side, with the neck for introducing and removing reaction liquid repositioned in another suitable location of the housing.

The reaction agent and the substances to be cultivated are introduced through the bottle neck 18, for example, by tilting the housing to a vertical or inclined position. The filling up of the housing can also be done when it is in a horizontal position. For example, one or more tubes (not shown in the drawings) can be placed in the neck extending into the housing to allow liquids or gases to be introduced or drained or allow the contents to be emptied from the housing without it having to be opened.

When an appropriate quantity of liquid and gas is introduced into the housing 11, the latter together with the trays 12 or the trays 12 alone (when not attached to the housing) are driven into rotation along the longitudinal axis LL of the housing under the action of the driving means 15 provided for this purpose. During their rotation, the trays 12 are dipped into the reaction liquid and during the ascending travel of the trays to a horizontal position, a determined quantity of reaction liquid is retained by the rims on the ascending side of each tray and is entrained along with the trays. The liquid in excess flows gradually over the rims and possibly through apertures or spaces between adjacent partitions of adjacent trays (in further embodiments described below). The liquid falls again to the lowest part of the housing and covers all the surfaces lower down.

In the example described above, the trays 12 are attached to the inner surface of the housing at their two longitudinal edges. It must be noted that the trays 12 can be attached to the housing at only one of their longitudinal edges, while the free longitudinal edge of each tray has raised rims 31 which project from both sides of the base sheet so as to form basins capable of retaining a quantity of reaction liquid as explained above. An advantageous arrangement consists in alternatingly attaching one longitudinal edge of the tray to the housing, then the opposite longitudinal edge of the next adjacent tray. The parallel arrangement of trays proves to be particularly simple to construct.

The trays may be rotated by half-turns in alternate directions in a cycling arrangement that may be particularly suited for culturing adherent cells. A rotation through at least 180° in one direction followed by a rotation through at least 180° in the opposite direction after return to the starting point allows a film of reaction agent to "wet" and momentarily remain for a determined interval of time on the opposite surfaces of the trays 12 and the interior surfaces of the housing and to cultivate adherent cells on these surfaces. A main condition for cultivating adherent cells is that they must deposit onto the surface of the trays under conditions where they can adhere to it. Only then can the cells divide and proliferate. Simply allowing the trays to dip into the liquid culture medium would not be sufficient by itself to ensure proper attachment of the cells. The described tray structure having rims for retaining fluid for an interval of time as the trays rotate in alternate directions to the horizontal position can effectively culture cells on both sides of the trays. The volume of liquid lifted during the tray rotation is determined by the volume formed by the height of the rims surrounding the surface of the tray dipping in the reaction liquid.

Figure 2B:
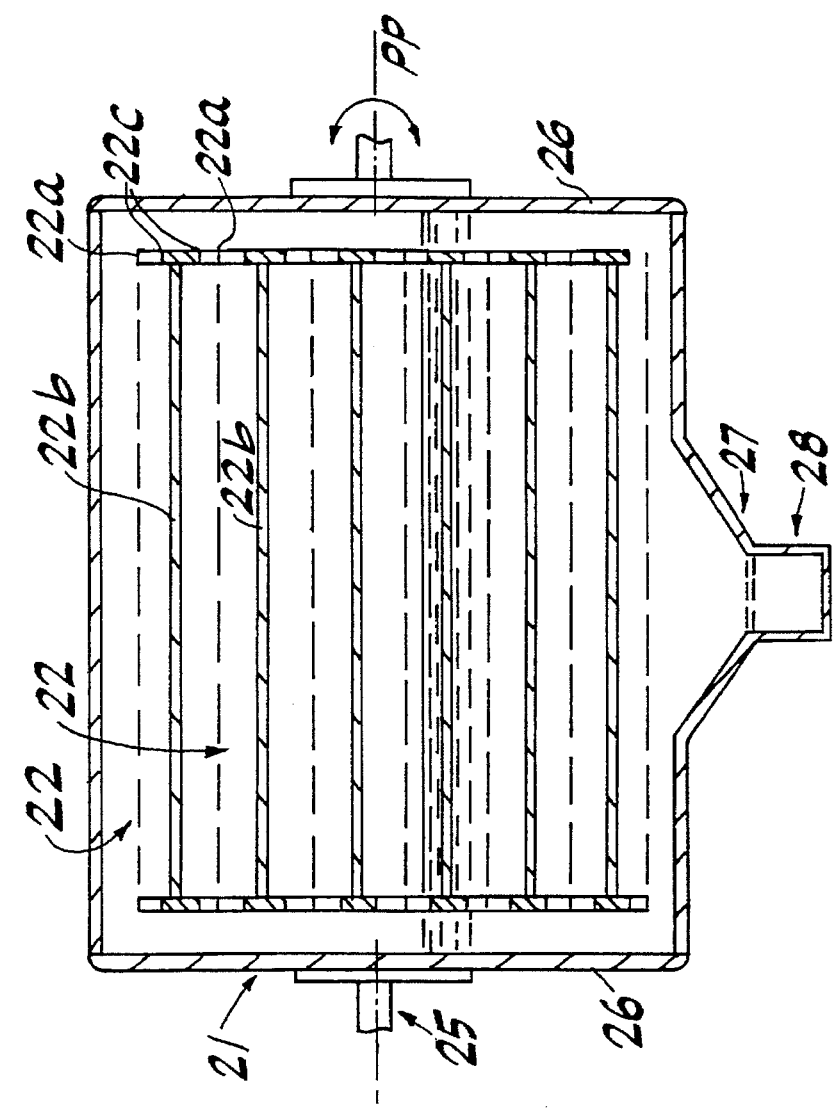
FIG. 2B is a side cross-sectional view thereof.
Figure 2A:
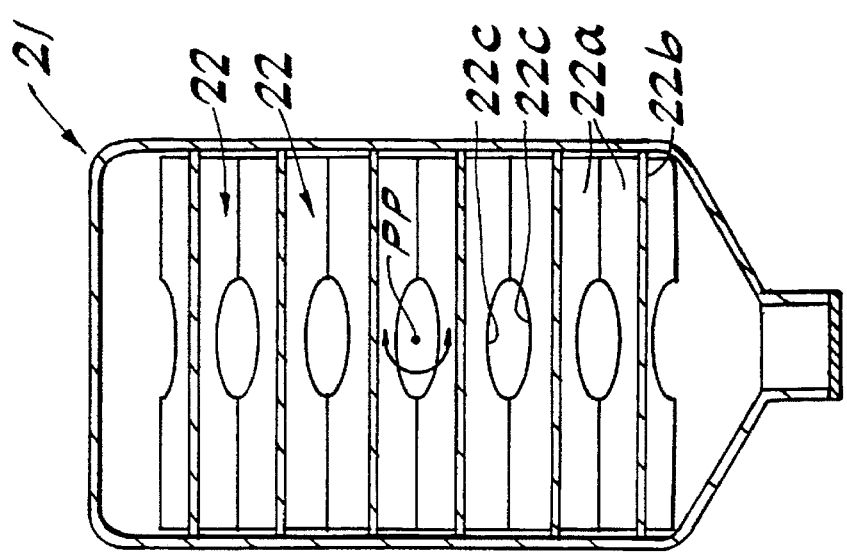
FIG. 2A is a front cross-sectional view of a second embodiment of the invention apparatus having stacked parallel trays attached to a rotatable housing.

In another embodiment shown in FIGS. 2A and 2B, the trays 22 are again fixed to the inner sides of the housing 21, such as by having their longitudinal edges secured in grooves or by attachment to the inner walls. However, in this embodiment, the trays have wall or rim sections of two different heights. A first rim section 22a of a given first height extends along the longitudinal sides (lengthwise in FIG. 2A) and part of the transverse sides (widthwise in FIG. 2B) of each tray. A second rim section 22c of a reduced second height is located at the center portion of the transverse sides of each tray. The trays 22 are arranged in a stacked configuration with the heights of abutting first rim sections defining a double spacing between the plane surfaces 22b of adjacent trays, while the reduced heights of the second rim sections define apertures that allow the flow of reaction liquid out from the lateral sides of the trays as they are rotated. A neck closure part 27 and bottleneck 28 allow the introduction and removal of liquid medium and gas phase. End walls 26 are sealingly mounted to the housing 21 to form the enclosed container. For culturing adherent cells, the bioreactor can be rotated by alternate half-turn rotations along the axis "PP" as described above to cultivate cells on both sides of the plane surfaces 22b of the trays.

Figure 3A:
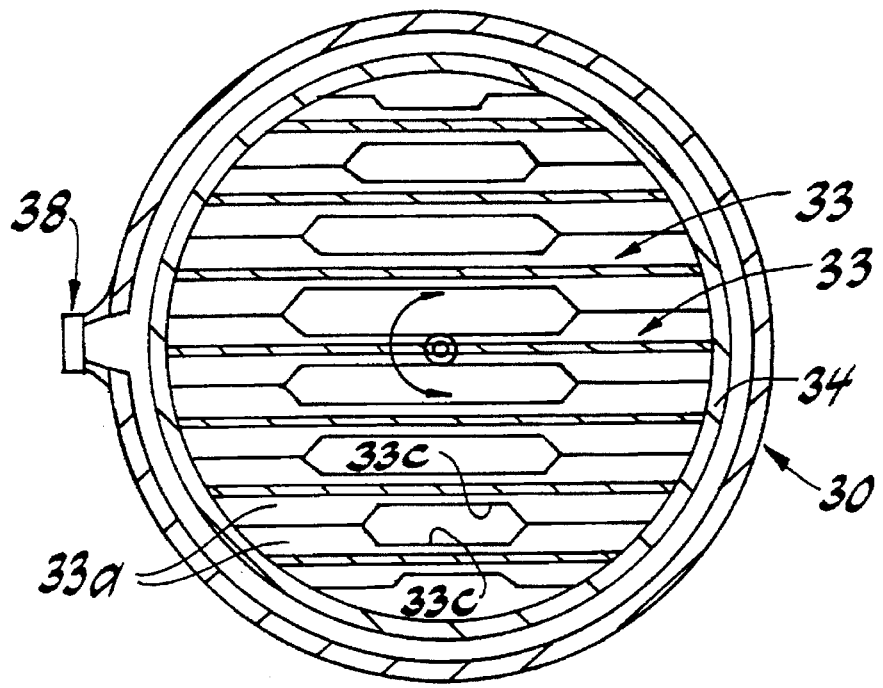
FIG. 3A is a front cross-sectional view of a third embodiment of the invention apparatus having stacked parallel trays fixed together for rotation within a stationary housing.
Figure 3B:
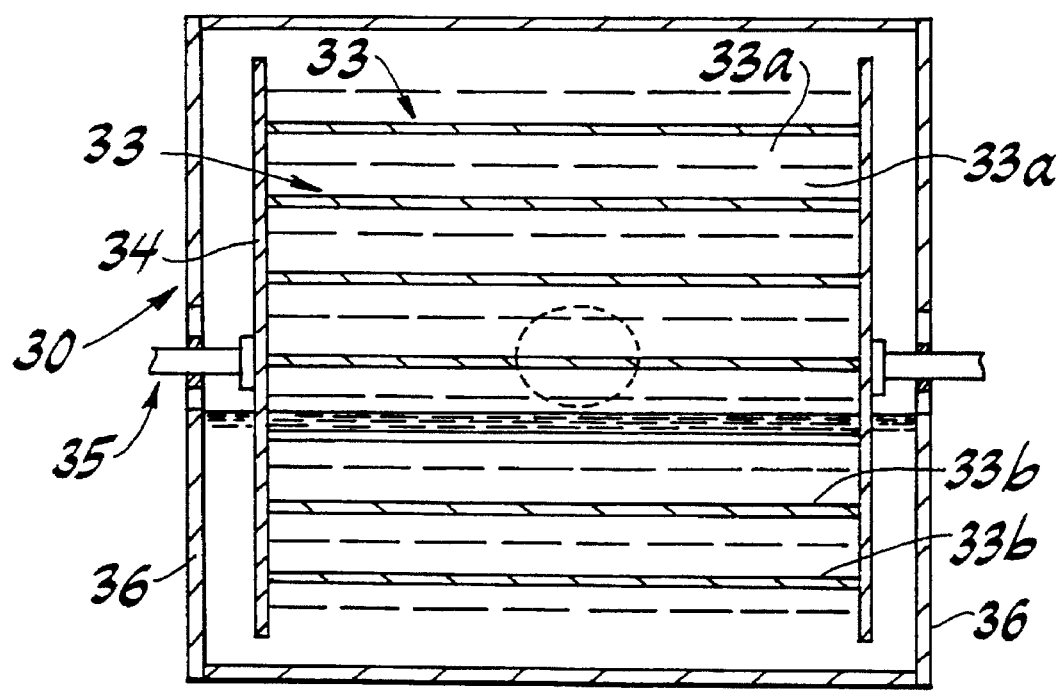
FIG. 3B is a plan cross-sectional view thereof.
Figure 3C:
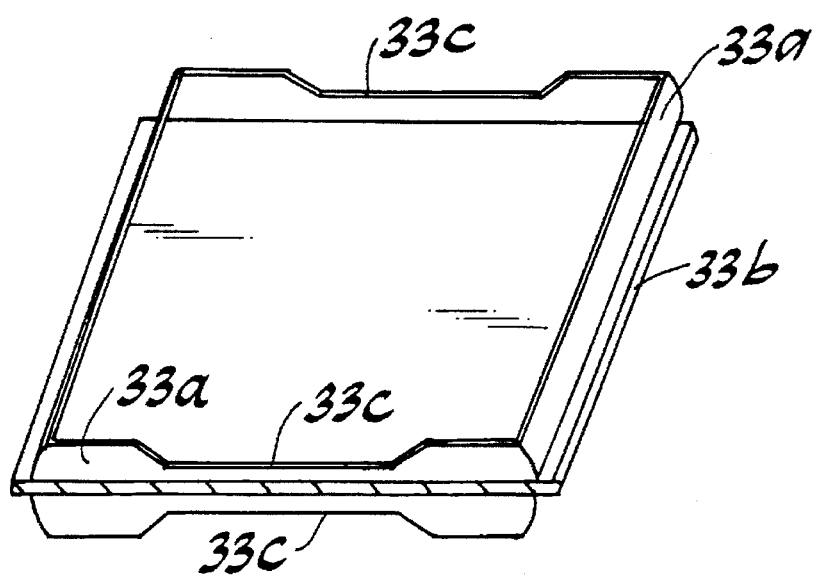
FIG. 3C shows a tray thereof in perspective view.

In FIGS. 3A to 3C, a third embodiment is shown having the trays 33 fixed to a frame 34 to form a unitary rotating body inside a stationary housing 30. The trays 33 are in stacked configuration and fixed to the frame 34 by their longitudinal edges. The rims include first rim sections 33a of a greater height that defines the double spacing between adjacent trays, and second rim sections 33c having a reduced height to form apertures to allow reaction liquid to flow out from the transverse sides of the trays as they are rotated. It is to be understood that the reduced-height rim sections may instead be positioned along the longitudinal sides of the trays. A bottleneck 38 allows the introduction and removal of liquid medium and gas phase. End walls 36 cover the ends of the housing 30 to form the enclosed container. FIG. 3C shows a detailed view of an individual tray. The frame 34 mounting the trays 33 is rotatable on an axle or shaft 35 along the longitudinal axis. For culturing adherent cells, the frame 34 can be rotated by alternate half-turn rotations as described above.

Figure 4:
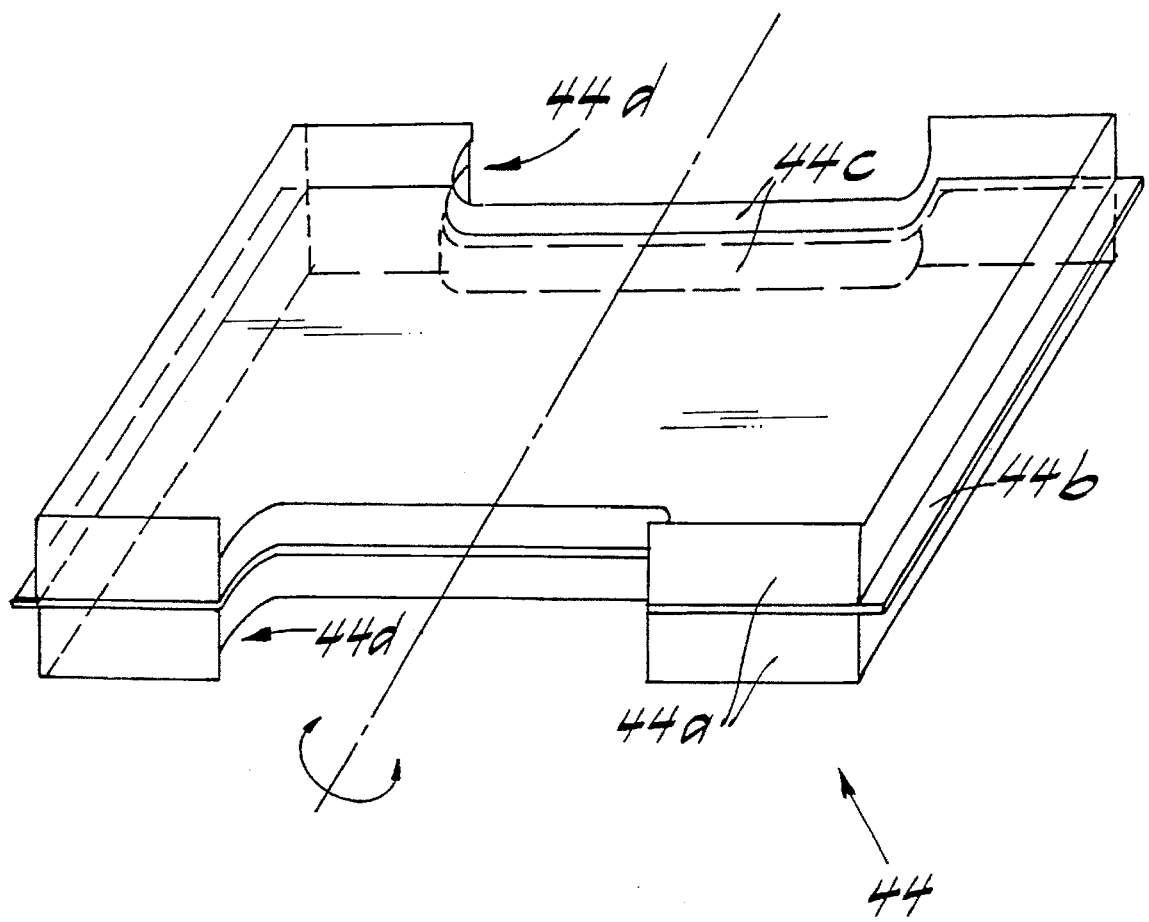
FIG. 4 shows a perspective view of an alternative form of tray having cutout sections for the flow of liquid medium.

In FIG. 4, an alternate form of a tray 44 is shown in perspective having first rim sections 44a, planar section 44b, reduced-height rim sections 44c, and indented cutout sections 44d for enhancing the draining of liquid medium from the trays as they are rotated. The tray 44 can be used in an embodiment similar to that shown in FIGS. 1A and 1B or in FIGS. 2A and 2B, wherein the trays are attached to the inner walls of the housing, or in the an embodiment similar to FIGS. 3A to 3C, wherein the trays are mounted to a frame rotatable within a stationary housing. The indented cutout sections 44d provide for drainage and movement of the liquid medium over the trays within the housing, while allowing the length of the trays to run the full length of the housing, thereby yielding even greater surface area for culturing.

Figure 5A:
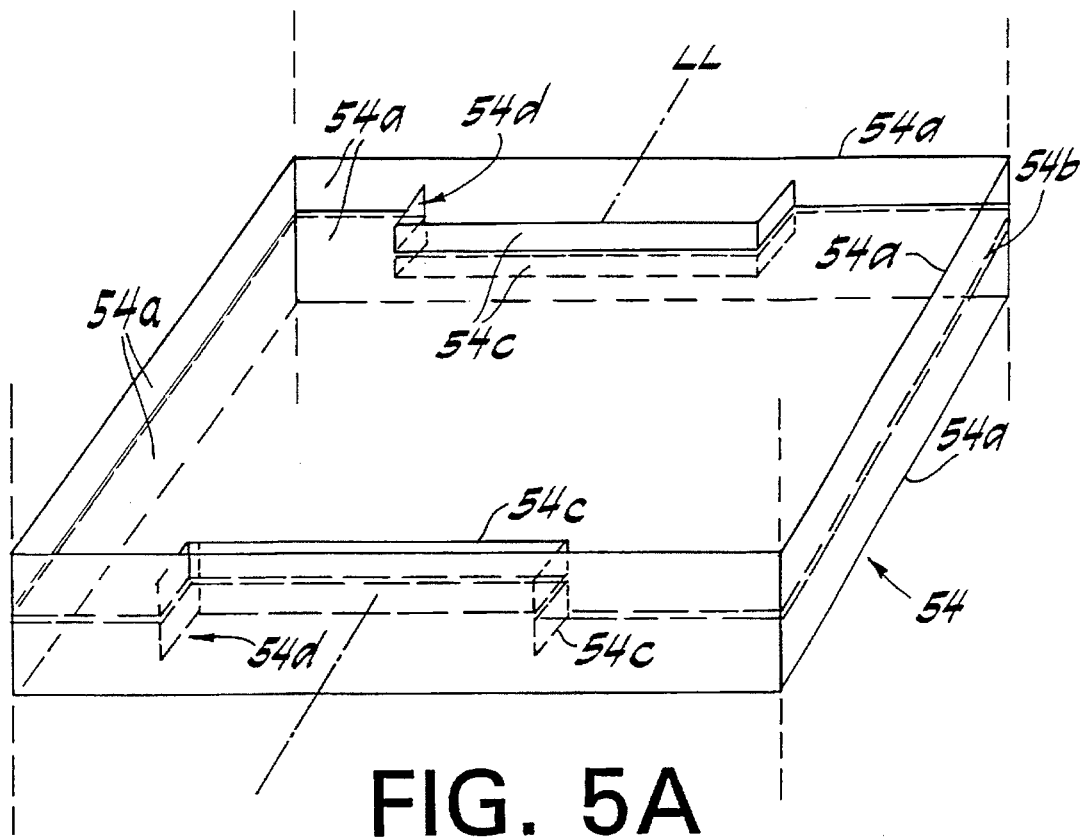
FIG. 5A is a perspective view of a tray for a fifth embodiment of the invention apparatus having the abutting rims of stacked parallel trays welded together to form an enclosed housing.
Figure 5B:
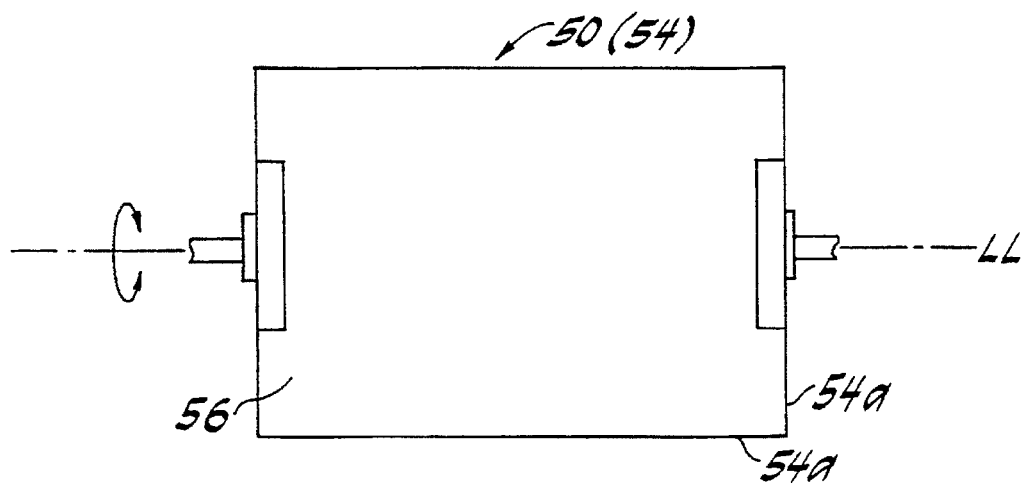
FIG. 5B is a plan cross-sectional view thereof.

In a further embodiment shown in FIGS. 5A and 5B, the trays 54 have the first rim sections 54a formed as solid plates which are sealingly welded to the first rim sections of the adjacent trays to form a flat external surface that replaces the need for a separate housing part. The trays 54 have reduced-height second rim sections 54c which are indented via cutout portions 54d to form passageways between the trays for the flow of liquid medium over the plates. The trays have rims on both sides of the planar base 54b so that both sides can retain reaction liquid, thereby increasing the amount of usable culturing surface area. The trays can be rotated on either the longitudinal axis LL or the transverse axis by any known driving means. Rotation through alternate half-turns allow the cultivation of cells on both sides of the trays. The housing (indicated by the numeral 50 in FIG. 5B) formed by the rims 54 is closed by plates 56 at both ends similar to those described previously, and a neck can be formed in either end plate but more preferably is formed on one side of the housing in the direction of the rotation axis in order to minimize wetting of the neck and risking contamination. The use of identically shaped trays which can simply be welded together to form an enclosed housing allow the manufacturing cost to produce such a unit to be greatly reduced.

Figure 6A:
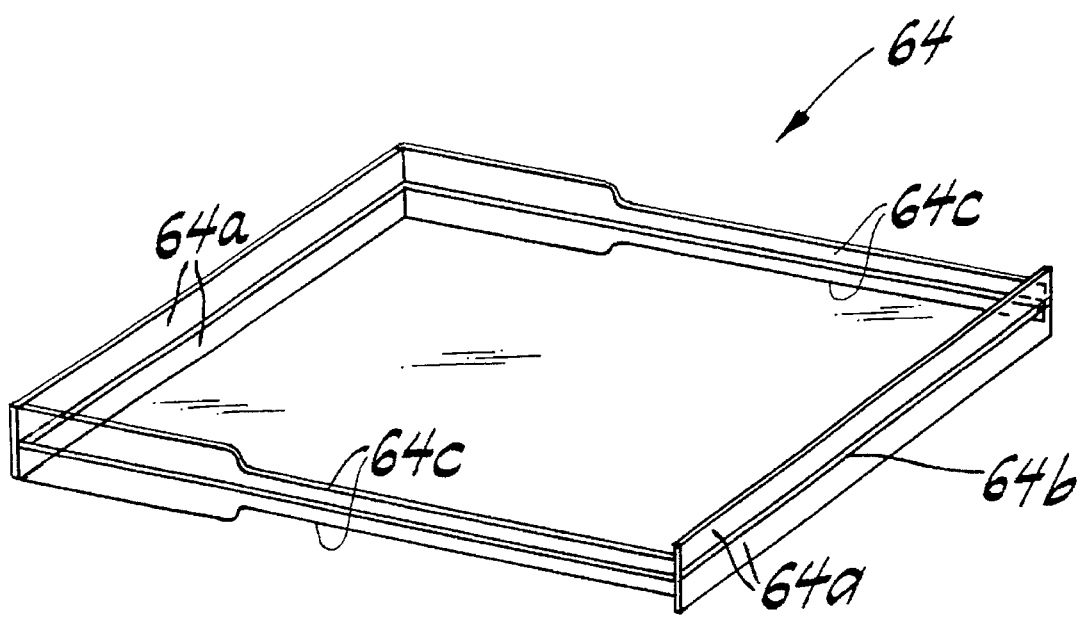
FIG. 6A is a perspective view of a tray for a sixth embodiment of the invention apparatus having abutting higher rims and asymmetrically positioned lower rims.
Figure 6B:
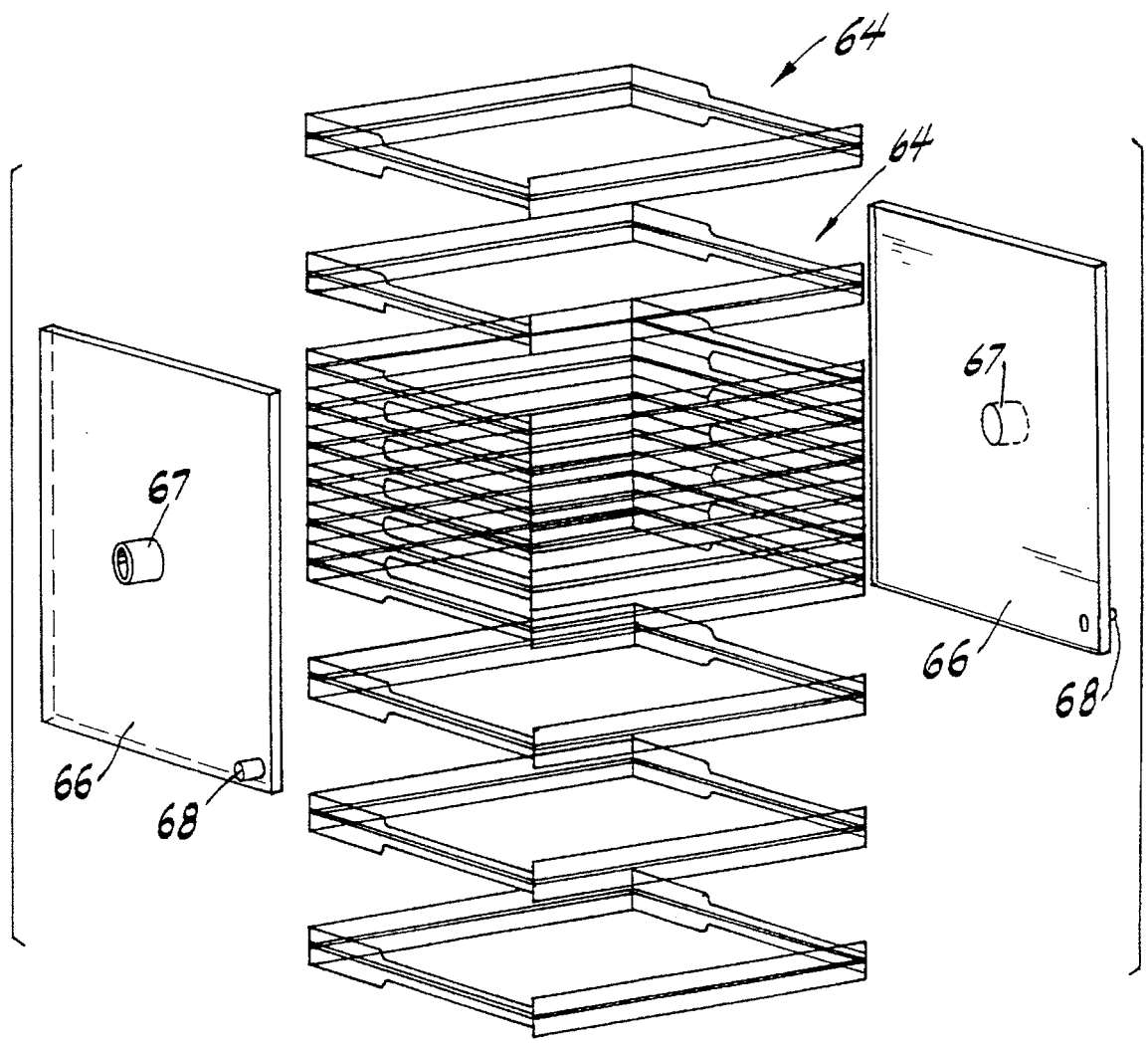
FIG. 6B is an exploded view of its parts to be assembled.
Figure 6C:
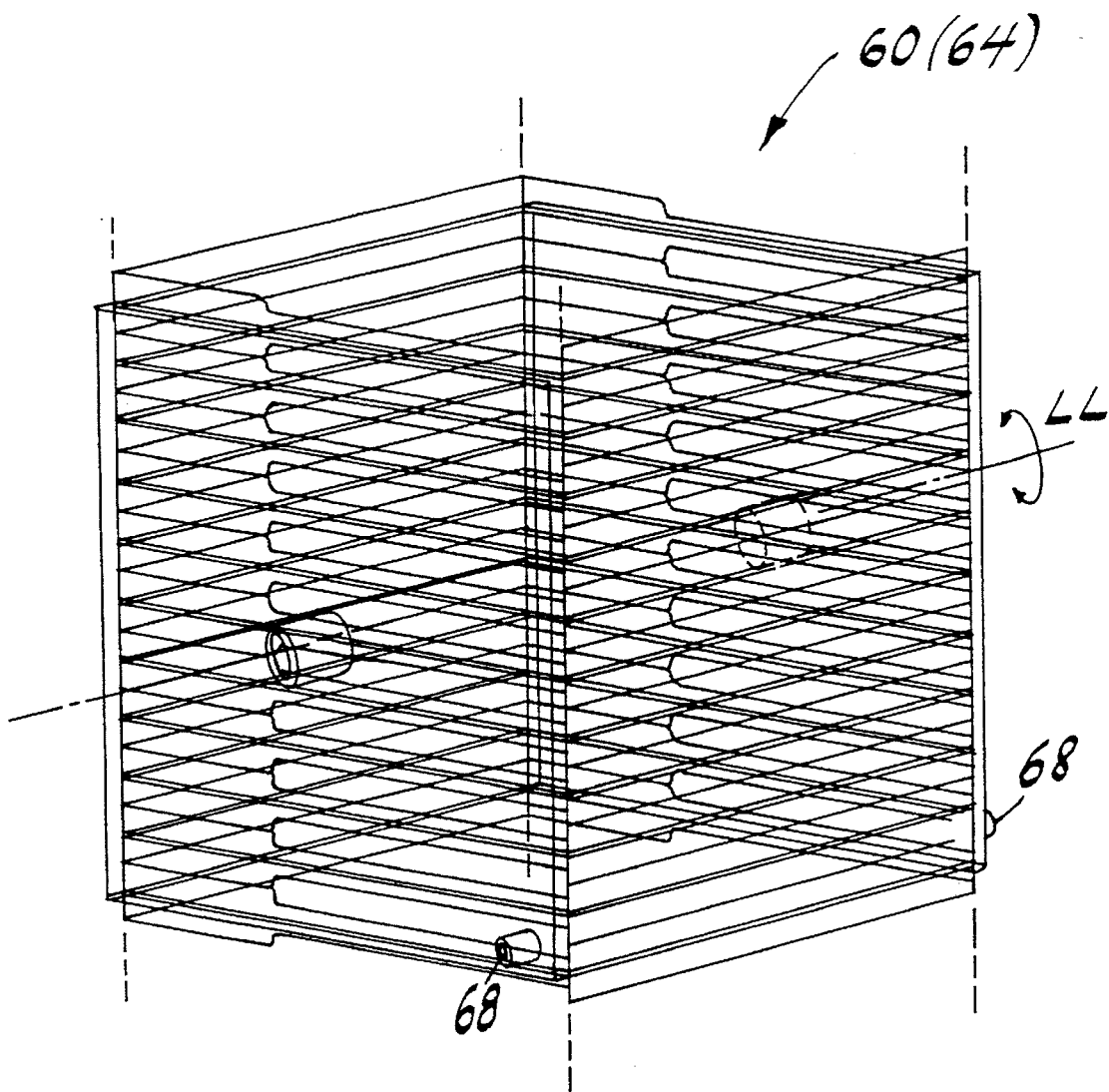
FIG. 6C is an assembled view thereof.

A further embodiment shown in FIGS. 6A, 6B and 6C again forms a bioreactor housing 60 by stacking trays 64 having first rims 64a on both sides of a planar base 64b which are welded together to form the outer walls of the housing, and second rims 64c of reduced height for allowing fluid flow from one side of the trays to the other. The first rims 64a extend on opposing longitudinal sides and over part of the transverse sides of the trays. The second rims 64c are positioned at one lateral end asymmetrically with respect to the rotational axis LL. End plates 66 are welded to the transverse sides in the direction of the rotational axis and create hollow walls at those sides for the fluid flow. Other end plates (not shown) are provided at the upper and lower ends to seal the housing completely. A pair of necks 67 are provided on opposite sides of the housing in the direction of the rotational axis LL. The necks 67 are used both as journals for the rotational driving mechanism of the bioreactor and also as inlet/outlet ports in the middle of the end plates 66. They are closed by filter caps which are equipped with bacterial air filters which allow full gas exchange while containing the biological matter. Additional inlet/outlet ports 68 are also provided at lower points of the end plates 66 for complete drainage. The inlet/outlet ports are connected via flexible tubing to a supply container for the reaction liquid or cell suspension medium. This allows the bioreactor to be filled or emptied without having to open it, which greatly reduces the risk of contamination. The inlet/outlet ports also allow several bioreactors to be connected together in cascade fashion to multiply the production rate and lower the unit labor costs.

The asymmetrical construction of the rims allows a much better drainage of the bioreactor during the cell or microorganism harvesting. The reaction liquid can freely flow from one chamber (formed by the walls and bases of adjacent trays) to another when the trays are tilted on end. Since the reduced-height rims 64c are positioned at one lateral end asymmetrically with respect to the rotational axis, all of the fluid can drain out through the drainage ports 68 when the trays are rotated vertically on that end.

In the above-described embodiments, the provision of rims and use of two sides of the trays rotated through the reaction medium allow the effective gas/liquid exchange area of the apparatus to be considerably increased for a given total volume of apparatus. The increased exchange area provides a greater surface for the culturing adherent cells or microorganisms. For non-adherent cells, microorganisms, microcarriers or microspheres, sufficient movement of liquid and gas phase contact are also ensured without an internal stirring system. The rotation of the trays provides excellent stirring and movement of the liquid in the apparatus, thereby providing a homogeneous distribution of liquid and greatly increasing the exchange and culture efficiency.

When adherent cells are cultivated within the housing, they can be harvested using conventional methods such as a proteolytic enzyme solution, e.g., trypsin, versen, or any other chelating agent which aims to detach cells from their support.

The rotating bioreactor is designed to allow equally the culture of adherent cells as well as suspension cells. It also allows adherent cell culture with microcarriers. In this case, all the inner surfaces provided to this end and the surface formed by the microcarriers can be used for cell growth.

Rotating the trays through half a turn in one direction and then in the other direction makes it possible to connect several apparatuses together while working. To this end, an orientation mark is advantageously provided on each apparatus, e.g., a reference mark, so as to ensure a well coordinated operation of the different apparatuses. This allows with the help of the tubes mentioned above, to introduce or drain liquid at any time, to change medium without having to open the housing and to take representative microcarrier samples in order to observe cell growth.

The apparatus according to the invention permits two types of culture to be carried out within the same bottle, viz., adherent cell or microorganism culture, with or without microcarriers. This significant and specific advantage of the invention thus allows only one type of bottle to be used, whatever the type of cells or microorganisms cultivated may be.

The arrangement of several trays makes it possible to substantially increase the culture surface for a constant volume. Thus, the apparatus permits the production of a large quantity of cells in a restricted total volume. The apparatus permits both the culture surface and the exchange surface to be substantially increased within a given volume. The increase in surface as compared to a conventional roller bottle or a fermentor can be higher than 1000%.

Another advantage of the apparatus according to the invention is that the culture conditions are kept independent of the size of the housing, the ratio between the volume of liquid used, the volume of the gas phase and the total culture or exchange surface being constant. The changeover from a low capacity housing to a housing of greater capacity can therefore be done without modifying the parameters ruling the culture.

The apparatus also permits a liquid phase to be concentrated by evaporation. The liquid exchange surface between the gas phase and the liquid phase allows, by circulating dry gas inside the housing or by sucking up the gas phase, to partially or entirely evaporate the liquid phase contained in the housing.

Although the invention has been described with reference to certain preferred embodiments, it will be appreciated that many other variations and modifications thereof may be devised in accordance with the principles disclosed herein. The invention, including the described embodiments and all variations and modifications thereof within the scope and spirit of the invention, is defined in the following claims.

I claim:

1. An apparatus for providing an enhanced liquid/gas exchange surface during culturing of cells, comprising:

(a) an enclosed housing for holding a volume of reaction liquid and a volume of gas therein, the housing extending in longitudinal and transverse directions thereof and having an inlet/outlet port for introducing and removing the reaction liquid therefrom;

(b) a stacked arrangement of a set of trays arranged in parallel inside the housing with a regular spacing between them and fixed together for rotation to contact the reaction liquid and gas alternately in rotation cycles, each of said trays having:

(i) a planar base with culturing surfaces on opposite planar sides thereof and lateral edges on opposing longitudinal and transverse sides thereof, (ii) first retaining rims extending continuously around at least said opposing longitudinal sides of the planar base and projecting a first height in opposing directions normal to the plane of the base toward the respectively adjacent trays in parallel with each said tray, said first height being equal to one-half of the spacing between adjacent trays such that the first retaining rims projecting in opposing directions of the adjacent trays abut each other, and (iii) second retaining rims continuing from said first retaining rims and extending over at least a portion of the opposing transverse sides of the planar base and projecting a second height lower than the first height in opposing directions normal to the plane of the base so as to define with said first retaining rims a shallow volume for retaining reaction liquid on the culturing surfaces of respective planar sides of the planar base for an interval of time when the set of trays is rotated through a horizontal position in one part of a rotation cycle while also forming openings on the opposing transverse sides between the trays for the flow of reaction liquid to drain out over the lower-height second retaining rims and expose the culturing surfaces to gas when the set of trays is rotated through a vertical position in another part of the rotation cycle, and (c) driving means coupled through the housing for rotating the set of trays about a rotational axis through the reaction liquid and gas contained in the housing.

2. An apparatus according to claim 1, wherein said planar base of each said tray has cutout portions surrounded by the second rim indented from the lateral edges on opposing sides of the base to allow reaction liquid to flow from one planar side of the trays to the other.

3. An apparatus according to claim 1, wherein said trays are fixed together to form a rotating body inside a stationary housing.

4. An apparatus according to claim 3, wherein said trays are fixed by their longitudinal edges to a frame coupled to said driving means through said housing.

5. An apparatus according to claim 1, wherein said trays are mounted to inner walls of the housing to be rotated together therewith.

6. An apparatus according to claim 1, wherein said first retaining rims extend entirely around the longitudinal sides and part of the transverse sides the trays, said planar base of each tray has cutout portions indented from the lateral edges on another part of the opposing transverse sides of the base, and said second retaining rims are arranged around said cutout portions, and said trays are arranged in a stacked configuration with the cutout portions and lower height of the second retaining rims defining apertures on the opposing transverse sides that allow the flow of reaction liquid from the planar sides of the trays as they are rotated.

7. An apparatus according to claim 1, wherein said driving means rotates said trays 180° in alternate directions through a horizontal position for culturing adherent cells on both sides of the tray bases.

8. An apparatus according to claim 1, wherein said second retaining rims are positioned on opposing transverse sides of the trays asymmetrically with respect to the rotational axis.

9. An apparatus according to claim 1, wherein said housing comprises a pair of end plates welded to the stacked arrangement of trays at the opposing transverse sides of the trays to form hollow spaces between the transverse sides and walls of the housing to allow fluid flow from said transverse sides into said housing.

10. An apparatus according to claim 9, wherein said second retaining rims are positioned toward one lateral end of the transverse sides in order to allow full drainage of the reaction liquid therefrom through inlet/outlet ports provided in said end plates at said one lateral end thereof.

11. An apparatus according to claim 10, wherein said end plates include a pair of necks provided on opposing transverse sides of the housing in the direction of the rotational axis which are used both as journals for said rotational driving means of the apparatus and also as inlet/outlet ports in the middle of said end plates.

12. An apparatus according to claim 1, wherein said housing is provided with a pair of inlet/outlet ports at opposing transverse sides thereof.

\* \* \* \* \*